United States Patent [19]

Dent

[11] Patent Number: 4,482,348
[45] Date of Patent: Nov. 13, 1984

[54] FITMENTS FOR INJECTION DEVICES

[75] Inventor: Hugh R. Dent, Chippenham, England

[73] Assignee: Sterimatic Holdings Limited, Tortola, British Virgin Isls.

[21] Appl. No.: 457,686

[22] Filed: Jan. 13, 1983

[30] Foreign Application Priority Data

Jan. 14, 1982 [GB] United Kingdom ............... 8201048

[51] Int. Cl.³ .............................................. A61M 5/00
[52] U.S. Cl. ................................. 604/198; 604/263
[58] Field of Search ............... 604/198, 263, 144, 156, 604/157, 136–139

[56] References Cited

U.S. PATENT DOCUMENTS

| | | | |
|---|---|---|---|
| 1,921,034 | 8/1933 | LaMarche | 604/157 |
| 3,134,380 | 5/1964 | Armao | 604/198 |
| 3,354,881 | 11/1967 | Bloch | 604/198 |
| 4,392,859 | 7/1983 | Dent | 604/263 X |

Primary Examiner—John D. Yasko
Attorney, Agent, or Firm—Young & Thompson

[57] ABSTRACT

In order to minimize the risk of infection when a large number of animals are injected with the same needle, an injecting gun is fitted with a sleeve which surrounds the needle. The sleeve comprises two telescoping tubes, and a detachable plastics cap incorporating a sponge impregnated with a sterilizing substance is fitted on the free end of the sleeve. The cap is provided with a twist off portion connected to the remainder of the cap by a thin-walled annular neck. The portion is separated from the remainder of the cap by twisting so as to form an aperture in the end wall of the cap, and an injection is then effected by applying the end of the cap to the proposed site of injection to cause the tubes to telescope so that the point of the needle moves through the sponge and passes through the aperture into the injection site.

23 Claims, 6 Drawing Figures

FITMENTS FOR INJECTION DEVICES

BACKGROUND OF THE INVENTION

This invention relates to fitments for injection devices of the kind in which injection liquid is delivered through a hollow needle. Such devices are used for injecting humans, animals, trees, fruit or vegetables, for example.

Farmers have for many years given routine oral drenches of anthelminthics to suppress the effects of intestinal and other parasitic worms in cattle, sheep and pigs. However, these drenches only become effective after a relatively long period. Although it has recently become possible to achieve the same effect in a much shorter space of time by injecting the animal, there has been a reluctance by farmers to use the new method. This is because it is not usual to sterilise the site of injection either before or after injection. Moreover the same needle is often used for injecting a large number of animals without sterilising the needle between each injection, in view of the large number of animals which have to be injected at one time, so that the site of injection often becomes infected leading to an abscess. Also, especially with sheep, there are several routine injections given to stop various clostridial complications, and each time the animal is injected it increases the risk of rejection of the carcass for human consumption due to abscesses.

Specification U.S. Pat. No. 2,080,688 discloses a fitment for injection devices of the kind referred to in which a sterilising substance is disposed in an enclosure at one end of the fitment for sterilising the point of the needle as it moves through the sterilising substance into the site of injection. However an aperture is provided in an end wall of the enclosure for the passage of the needle into the injection site, and the sterilising substance may become contaminated by way of this aperture prior to an injection being effected. It is an object of the invention to provide such an injection device with increased resistance to contamination of the sterilising substance.

SUMMARY OF THE INVENTION

According to the invention there is provided a fitment for attachment to an injection device of the kind in which injection liquid is delivered through a hollow needle, the fitment being provided to sterilise the needle as it is passed into the site of injection, and comprising an enclosure incorporating means for sterilising the needle as the needle is moved therethrough into the injection site, the enclosure having an end wall which is adapted to have an integral removable portion separated therefrom by rupturing the material of the end wall so as to form an aperture in the end wall through which the point of the needle may pass into the injection site.

Whilst the word "sterilising" is used in this specification in the sense of killing microorganisms, such as bacteria or viruses, it should be understood that it is not essential that all microorganisms are killed, that is to say that the needle is rendered absolutely sterile. The sterilising means may, for example, comprise a sterilising substance in the form of a liquid, gel or powder.

The sterilising means is prevented from being contaminated by the removable portion which may be separated from the remainder of the end wall just before an injection or the first of a series of injections is to be effected so as to provide the required aperture for the point of the needle to pass through towards the site of injection.

The removable portion may be attached to the remainder of the end wall by a substantially annular weakened region which is adapted to be ruptured in order to separate the removable portion. In a preferred embodiment of the invention the removable portion is adapted to be grasped manually and to be separated from the remainder of the end wall by twisting. For example the removable portion may be attached to the remainder of the end wall by a thin-walled annular neck constituting said weakened region. When this neck is ruptured by twisting the removable portion the removable portion will become separated from the remainder of the end wall and may be discarded leaving an aperture in the end wall for the needle.

In order to enable relative movement between at least the leading portion of the needle and the enclosure, the fitment conveniently also includes a first part for attachment to the injection device and a second part connected to the first part so as to be reciprocable relatively thereto in the direction of the length of the needle, the enclosure being carried on the second part and lying on the longitudinal axis of the needle when the fitment is attached to an injection device, whereby, in use, when an injection is effected by placing the second part against the site of injection and applying pressure to the injection device in a direction towards the injection site, relative movement takes place between the first and second parts so as to enable the point of the needle to move through the sterilising means into the injection site. Spring means may be provided to bias the relatively movable parts away from one another.

The enclosure may be in the form of a cap which is easily attachable to, and detachable from, the second part, for example by means of an externally screwthreaded portion of the enclosure which is received within an internally screwthreaded portion of the second part. This provides ease of replacement of the enclosure by an enclosure incorporating fresh sterilising means. The cap may be provided with one or more outwardly extending winged flanges thereon as an aid to detaching the cap from the second part. The sterilising means may be constituted by a body of absorbent material impregnated with sterilising substance.

The invention also provides a method of performing an injection using an injection device of the kind in which injection liquid is delivered through a hollow needle and a fitment comprising an enclosure incorporating sterilising means attached to the injection device, the method comprising separating an integral removable portion from an end wall of the enclosure by rupturing the material of the end wall so as to form an aperture in the end wall, applying the injection device to the site of injection, and moving the point of the needle through the sterilising means and into the site of injection by way of the aperture in the end wall.

Furthermore the invention provides a fitment for attachment to an injection device of the kind in which injection liquid is delivered through a hollow needle, the fitment including a collapsible sleeve for surrounding the needle, wherein the sleeve comprises two telescoping tubes, one of which is adapted for attachment to the injection device and the other of which extends beyond the point of the needle when the fitment is fitted to the device and the sleeve is fully extended, spring means biasing the telescoping tubes into the fully extended position, and guide means within the sleeve defining a bore which tapers in the direction of injecting movement of the needle for guiding movement of the needle within the sleeve whereby, in use, when an injection is effected by placing said other tube against the site of injection and applying pressure to the injection device in a direction towards the injection site, the sleeve is caused to collapse with the tubes telescoping against the action of the spring so as to enable the point of the needle to pass into the injection site, and the sleeve subsequently reassumes its extended position on release of said pressure when the needle is withdrawn from the injection site.

Complementary formations are preferably provided on the telescoping tubes to prevent relative rotation of the tubes.

BRIEF DESCRIPTION OF THE DRAWINGS

In order that the invention may be more fully understood, reference will now be made, by way of example, to the accompanying drawings, in which.

DETAILED DESCRIPTION OF THE DRAWINGS

Figure 1:
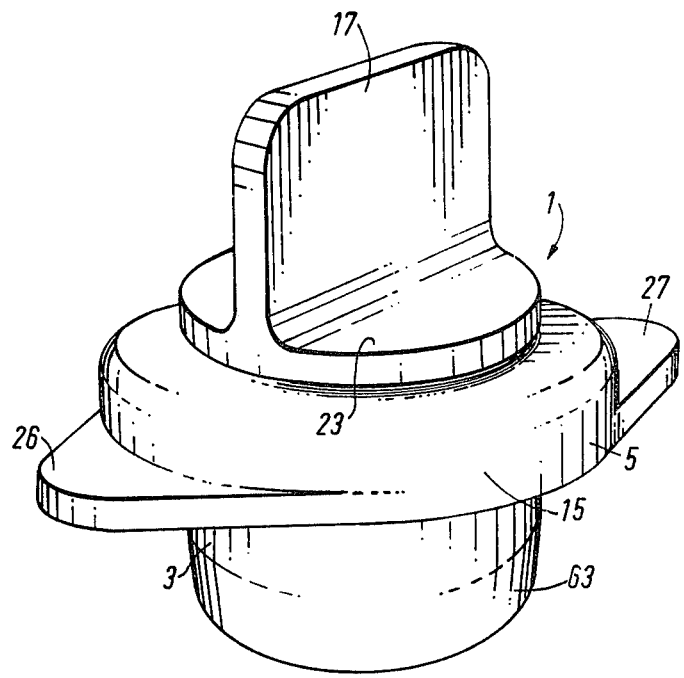
FIG. 1 is a perspective view of a plastics cap forming part of a fitment in accordance with the invention.

The plastics cap 1, which is shown on an enlarged scale in FIG. 1, is made of a material such as polypropylene or polyethylene and is formed by injection moulding in two parts, namely a cup-shaped body part 3 and a top part 5. The rim of the body part 3 is formed with an outwardly projecting flange 7 (see FIGS. 2 and 3) for engaging within an annular recess 9 in the inner surface of the top part 5 so as to provide a snap coupling between the two parts 3, 5 which together provide an enclosure 11 for a sponge 13 impregnated with a sterilising liquid. The parts 3 and 5 are connected together permanently by sonic welding.

Figure 3:
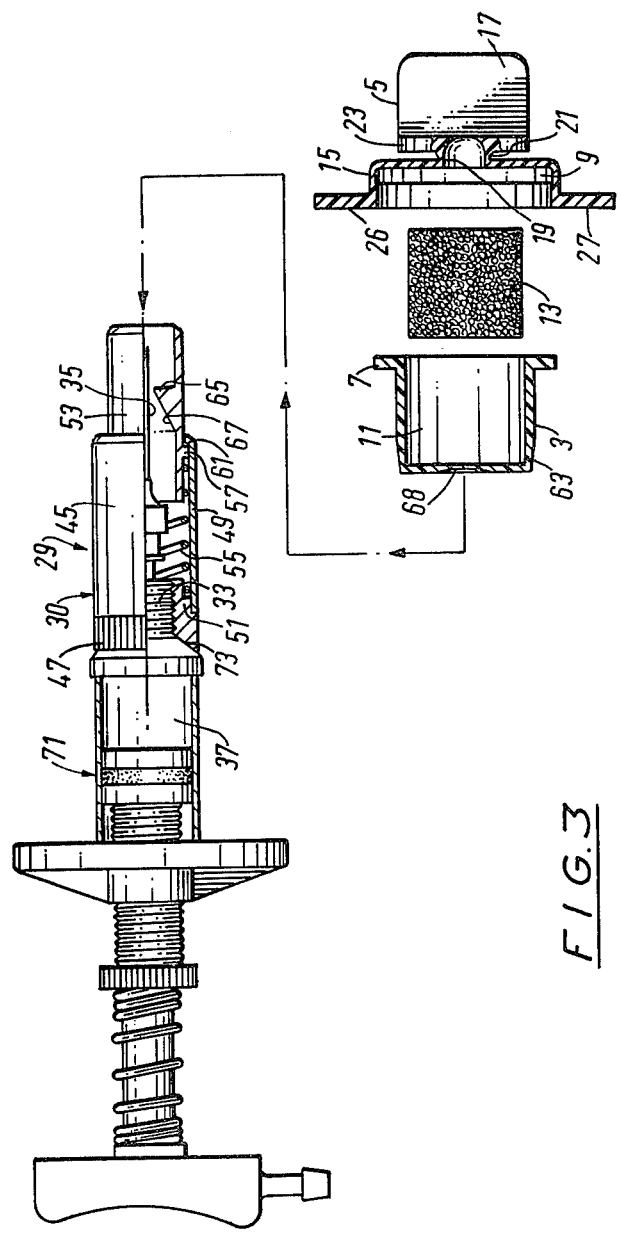
FIG. 3 is an exploded sectional view of the cap of FIG. 1 and a partially sectioned view of the remainder of the fitment, attached to a disposable syringe.

Referring to FIG. 3, the top part 5 of cap 1 comprises a dish-shaped end wall 15 having a twist-off portion 17 attached thereto. A recess 19 extends through the end wall 15 into the twist-off portion 17 and is surrounded by a thin-walled annular neck 21 connecting the twist-off portion 17 to the end wall 15. As may be seen in FIG. 1, the twist-off portion 17 is constituted by a circular disc 23 integrally formed with an upstanding tab 25 which may be grasped between the finger and thumb in order to twist the twist-off portion 17 in relation to the remainder of the cap 1 and to thereby separate the twist-off portion 17 from the end wall 15 at the neck 21. The end wall 15 is provided with outwardly extending winged flanges 26 and 27 for ease in fitting the cap to, and removing it from, the remainder of the fitment.

Figure 2:
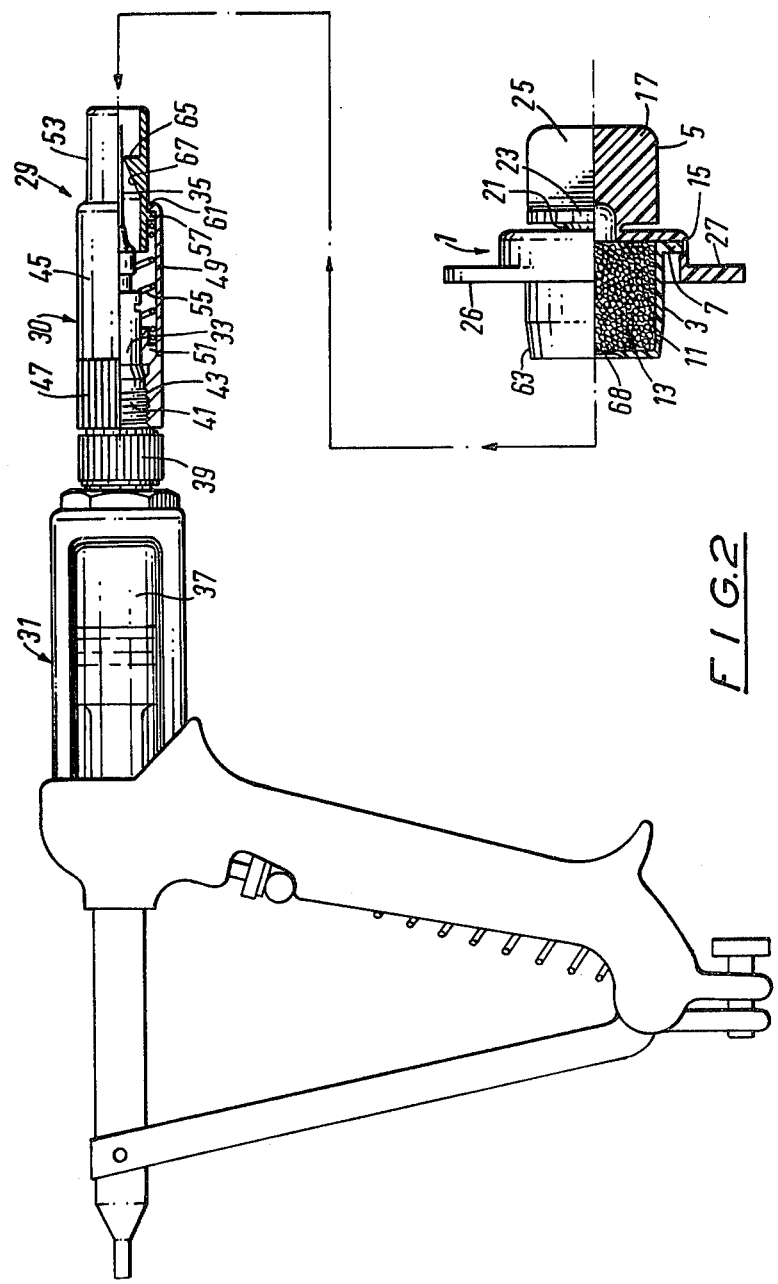
FIG. 2 is a partially sectioned view of the cap of FIG. 1 and of the remainder of the fitment, attached to an injection gun.

FIG. 2 shows the fitment 29, which includes a sleeve 30 in addition to the cap 1, connected to an injecting gun 31 of the type used for injecting cattle, sheep or pigs. The gun 31 includes a needle connecting body 33, a hollow metal needle 35 and a reservoir 37 for injection liquid. The sleeve 30 is preferably made of a plastics material which is more hard-wearing than the material of the cap, and may, for example, be made of an ABS plastics or polycarbon. A metal adaptor ring 39 is screwed on to the needle connecting body 33 and is itself provided with an external screwthread 41 for engaging an internal screwthread 43 within the sleeve 30. The sleeve 30 includes a first tube 45 comprising a collar 47 defining the internal screwthread 43 and having a milled outer surface, and a body portion 49 which is a push-fit on a shoulder 51 on the collar 47. In addition the sleeve 30 includes a second tube 53 which is telescopically slidable within the first tube 45 and is biased into its extended position by a return spring 55 within the body portion 49 acting between an annular flange 57 on the second tube 53 and the shoulder 51 on the collar 47. The end of the second tube 53 is retained within the first tube 45 by the flange 57 bearing against an inturned rim 61 on the end of the body portion 49.

The cap 1 is an interference fit on the end of the sleeve 30, the body part 3 of the cap 1 being tightly received within the free end of the second tube 53 and the outer surface of the second tube 53 itself being gripped by the rim of the dish-shaped end wall 15 of the cap 1. The body part 3 is tapered at 63 so as to make it easier to fit into the end of the second tube 53. Furthermore the second tube 53 is provided with an internal annular shoulder 65 defining a tapering bore 67 for guiding the needle 35 when an injection is being performed. Although not shown in FIGS. 1 and 2 the end wall 68 of the body part 3 is provided with a weakened central portion which may be pierced by the needle 35 when an injection is effected.

FIG. 3 shows a similar fitment 29 to that shown in FIG. 2 connected to a disposable plastics syringe 71 such as might be used for injecting humans or animals. However, in this case, an adaptor ring 39 is not required and the collar 47 is not provided with an internal screwthread but is a force fit on the needle connecting body 33. Furthermore the collar 47 tapers inwardly at 73 in order to make it easier to fit to the needle connecting body 33.

In use of the gun 1 or syringe 71 to inject an animal, it is first ensured that the reservoir 37 contains a sufficient quantity of injection liquid, that a needle 35 is connected to the needle connecting body 33 and that the sleeve 30 is fitted to the gun 1 or syringe 71. A cap 1 containing a sponge 13 impregnated with sterilising liquid is then fitted to the end of the sleeve 30, with the result that the needle 35 punctures the weakened central portion of the end wall 68 of the body part 3 and comes to rest with its point buried within the sponge 13. Immediately prior to an injection being effected, the twist-off portion 17 is twisted in relation to the remainder of the cap 1 so as to cause the thin-walled annular neck 21 to be ruptured and the twist-off portion 17 to be separated from the end wall 15 leaving a small aperture in the centre of the end wall 15.

In order to perform the actual injection the apertured end wall 15 of the cap 1 is applied to the proposed site of injection on the animal, and pressure is applied to the gun 1 or syringe 71 in the direction towards the animal. This causes the tubes 45, 53 to telescope so that the point of the needle 35 moves through the impregnated sponge 13 and then passes through the aperture in the end wall 15 of the cap 1. The needle 35 is thereby cleaned and coated with a layer of sterilising liquid prior to its penetrating the skin. The size of the aperture in the end wall 15 is such that the layer of sterilising liquid on the needle 35 is not wiped off as the point of the needle 35 passes through the aperture, so that the action of the needle 35 puncturing the skin will serve to transfer sterilising substance to the skin thereby sterilising the site of the injection. When the needle 35 has been pushed through the skin to the required depth the gun 1 or syringe 71 is operated to administer the required dose of injection liquid through the needle 35.

As the needle 35 is withdrawn after the dose has been administered, the second tube 53 is caused to return to its extended position by the return spring 55 so that the point of the needle 35 passes back into the sponge 13, thereby again cleaning the point of the needle 35 and coating it with a layer of sterilising liquid. The injection has then been completed and the gun 1 or syringe 71 may be moved away from the skin of the animal. The gun 1 or syringe 71 can then be used for performing a second injection without any further adjustment having to be made. If desired a large number of injections may be made using the same needle 35 and the same sterilising cap 1 without appreciably increasing the risk of infection. Alternatively the sterilising cap 1 may be replaced by a fresh sterilising cap after each injection or each series of injections has been effected. In the case of the disposable syringe shown in FIG. 3 the complete syringe may be discarded after each injection or each series of injections.

The sterilising cap 1 is readily replaceable by grasping it by the winged flanges 26 and 27 and pulling it off the end of the sleeve 30 so as to enable a new sterilising cap to be fitted to the sleeve 30 in the manner previously described. The sponge 13 impregnated with sterilising liquid is prevented from being contaminated by the atmosphere by the twist-off portion 17 until that portion is separated from the remainder of the cap 1 and discarded immediately prior to an injection being effected.

In a modification of the sterilising cap 1 described above with reference to the drawings the cross-section of the recess 19 is enlarged and the sponge 13 impregnated with sterilising liquid is caused to project through the enlarged aperture which is left on removal of the twist-off portion 17 so that a portion of the sponge 13 contacts the skin as an injection is effected thereby transferring further sterilising liquid to the site of injection.

Figure 4:
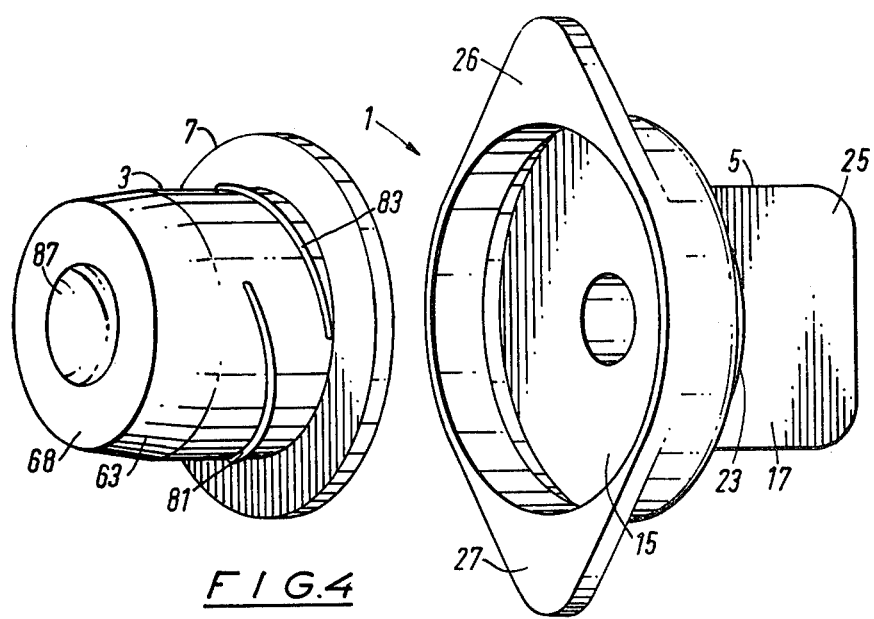
FIG. 4 is an exploded perspective view of an alternative form of cap.
Figure 5:
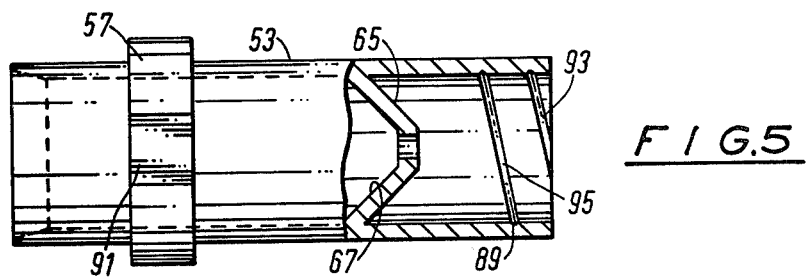
FIG. 5 is a side view, partly in section, of part of a telescoping sleeve to which the cap of FIG. 4 may be fitted.
Figure 6:
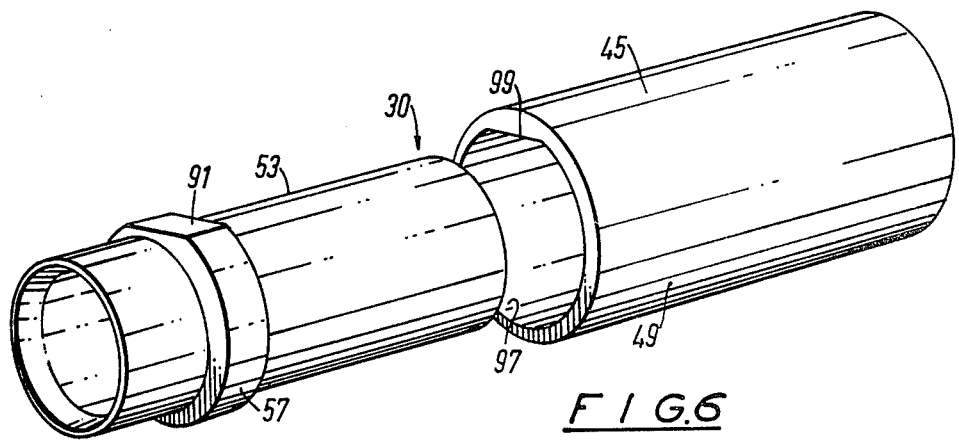
FIG. 6 is an exploded perspective view of the telescoping sleeve which is partially shown in FIG. 5.

FIGS. 4 to 6 show an alternative form of fitment in accordance with the invention for fitting to an injecting gun of the type shown in FIG. 2 or a syringe of the type shown in FIG. 3. Those parts of this embodiment which correspond to parts of the embodiments of FIGS. 1 to 3 have been indicated by the same reference numerals in FIGS. 4 to 6 as have the corresponding parts in FIGS. 1 to 3, and the following description is therefore concerned with the main differences between this embodiment and the arrangements previously described.

The cap 1 which is shown in FIG. 4 with its parts 3 and 5 separated differs from the cap 1 previously described with reference to FIGS. 1 and 3 substantially only in the provision of a two-start screwthread 81 on the body part 3 for attachment of the cap 1 to the end of the sleeve 30. The screwthread 81 comprises two separate thread portions 83 and 85 each of which extends slightly more than half the way round the periphery of the body part 3, the thread portions 83 and 85 being arranged relative to one another so that they overlap at both ends. The weakened central portion 87 of the end wall 68 of the body part 3 is visible in FIG. 4.

FIG. 5 shows only the second tube 53 of a sleeve 30 to which the cap 1 may be fitted. This second tube 53 differs from the second tube 53 described with reference to FIGS. 1 to 3 in that a two-start internal screwthread 89 is provided at the end of the tube 53 to which the cap is to be fitted, in that a flat 91 is provided on the annular flange 57 (see FIG. 6) and that the internal annular shoulder 65 is of a slightly different shape. The internal screwthread 89 comprises two separate thread portions 93 and 95 which are of substantially complementary configuration to the portions 83 and 85 of the external screwthread 81 on the cap 1 except that each portion 93,95 has a slightly greater arcuate extent than the corresponding portion 83,85. It will be appreciated that the provision of complementary screwthreads 81 and 89 on the cap 1 and the sleeve 30 enables the cap 1 to be fitted to the end of the sleeve 30 in a particularly secure manner so that there is no danger of the cap 1 being forced off the end of the sleeve 30 when an injection is effected.

The first and second tubes 45 and 53 of the sleeve 30 are shown separated from one another in FIG. 6 with the second tube 53 being shown as though it were about to be pushed into the first tube 45 until the annular flange 57 contacts the inturned rim (not shown) at the far end of the tube 45. The bore 97 within the first tube 45 is provided with a flat 99 which extends along the complete length of the tube 45 as far as the inturned rim. Thus, when the second tube 53 is fitted into the first tube 45, the flat 91 on the second tube 53 co-operates with the flat 99 within the bore 97 of the first tube 45 so as to prevent the second tube 53 from rotating within the first tube 45 when a cap is screwed into the threaded end of the second tube 53.

I claim:
1. An accessory for use with an injection device of the kind in which injectate is delivered through a hollow needle, the accessory being provided to sterilise the needle of the injection device as the needle is moved therethrough and comprising an enclosure having an end wall which incorporates an integral removable portion attached to the remainder of the end wall by a substantially annular weakened region which is capable of being ruptured in order to separate the removable portion so as to form an aperture in the end wall through which the point of the needle of the injection device may pass, the enclosure incorporating means for sterilising the needle as it is moved therethrough.

2. An accessory according to claim 1, wherein the removable portion is adapted to be grasped manually and to be separated from the remainder of the end wall by twisting.

3. A fitment according to claim 2, wherein the removable portion is attached to the remainder of the end wall by a substantially annular neck constituting said weakened region.

4. A fitment according to claim 1 wherein the enclosure is formed by a cup-shaped body part and a top part connected to the body part so as to close off the enclosure.

5. A fitment according to claim 4, wherein the body part is formed with an outwardly projecting flange for engaging within an annular recess in the inner surface of the top part so as to provide a snap coupling between the two parts.

6. A fitment according to claim 4, wherein the top part is connected to the body part by sonic welding.

7. A fitment according to claim 1, wherein the sterilising means is constituted by a body of absorbent material impregnated with sterilising substance and contained within the enclosure.

8. A fitment according to claim 1, wherein a wall of the enclosure has a weakened portion which may be perforated by the needle to enable the needle to be moved through the sterilising means.

9. A fitment according to claim 1, wherein the enclosure is adapted to be removably fitted to the end of tube.

10. A fitment according to claim 9, wherein the enclosure is formed with an external screwthread.

11. A fitment according to claim 1, wherein the enclosure is formed with outwardly extending winged flanges.

12. A fitment according to claim 1, wherein the accessory further includes a first part for attachment to the injection device and a second part connected to the first part so as to be reciprocable relatively thereto in the direction of the length of the needle, the enclosure being carried on the second part and lying on the longitudinal axis of the needle when the accessory is attached to an injection device, whereby, in use, when an injection is effected by placing the second part against the site of injection and applying pressure to the injection device in a direction towards the injection site, relative movement takes place between the first and second parts so as to enable the point of the needle to move through the sterilising means into the injection site.

13. A fitment according to claim 12, wherein the first and second parts are constituted by two telescoping tubes.

14. A fitment according to claim 13, wherein complementary formations are provided on the telescoping tubes about the needle axis to prevent relative rotation of the tubes.

15. A fitment according to claim 12, wherein spring means are provided to bias the relatively movable parts away from one another.

16. An accessory according to claim 12, wherein the enclosure is attached to the second part by means of an externally screwthreaded portion of the enclosure which is received within an internally screwthreaded portion of the second part.

17. A fitment for attachment to an injection device of the kind in which injection liquid is delivered through a hollow needle, the accessory including a collapsible sleeve for surrounding the needle, wherein the sleeve comprises two telescoping tubes, one of which is adapted for attachment to the injection device and the other of which extends beyond the point of the needle when the accessory is fitted to the device and the sleeve is fully extended, spring means biasing the telescoping tubes into the fully extended position, and guide means within the sleeve defining a bore which tapers in the direction of injecting movement of the needle for guiding movement of the needle within the sleeve whereby, in use, when an injection is effected by placing said other tube against the site of injection and applying pressure to the injection device in a direction towards the injection site, the sleeve is caused to collapse with the tubes telescoping against the action of the spring so as to enable the point of the needle to pass into the injection site, and the sleeve subsequently reassumes its extended position on release of said pressure when the needle is withdrawn from the injection site.

18. An accessory according to claim 17, wherein complementary formations are provided on the telescoping tubes about the needle axis to prevent relative rotation of the tubes.

19. An accessory according to claim 18, wherein the complementary formations comprise a flat on the outer surface of the inner of the two tubes which co-operates with a flat on the inner surface of the outer of the two tubes.

20. An accessory according to claim 17, wherein the free end of said other tube is internally screwthreaded.

21. An injection device provided with an accessory according to claim 1.

22. A method of sterilising the needle of an injection device of the kind in which injectate is delivered through a hollow needle, using an accessory comprising an enclosure incorporating means for sterilising the needle as the needle is moved therethrough, the method comprising separating an integral removable portion from an end wall of the enclosure by rupturing the material of the end wall in a substantially annular weakened region so as to form an aperture in the end wall, and moving the point of the needle through the sterilising means within the enclosure and through the aperture in the end wall.

23. An accessory for use with an injection device of the kind in which injectate is delivered through a hollow needle, the accessory being provided to sterilise the needle of the injection device as the needle is moved therethrough and comprising an enclosure having an end wall which is adapted to have an integral removable portion separated therefrom by rupturing the material of the end wall in a predetermined region so as to form an aperture in the end wall through which the point of the needle of the injection device may pass, the enclosure incorporating means for sterilising the needle as it is moved therethrough.

* * * * *